United States Patent [19]

Ehnström

[11] Patent Number: 4,460,687
[45] Date of Patent: Jul. 17, 1984

[54] FERMENTATION METHOD

[75] Inventor: Lars K. J. Ehnström, Tullinge, Sweden

[73] Assignee: Alfa Laval AB, Tumba, Sweden

[21] Appl. No.: 532,042

[22] Filed: Sep. 14, 1983

Related U.S. Application Data

[63] Continuation-in-part of Ser. No. 246,305, Mar. 23, 1981, abandoned, which is a continuation-in-part of Ser. No. 3,939, Jan. 16, 1979, abandoned.

[51] Int. Cl.³ .............................................. C12P 7/06
[52] U.S. Cl. ..................................... 435/161; 435/162; 435/813
[58] Field of Search ............... 435/161, 162, 165, 256, 435/813; 426/31, 53, 429, 431, 493, 494

[56] References Cited

U.S. PATENT DOCUMENTS

| | | | |
|---|---|---|---|
| 504,074 | 8/1893 | Bradley et al. | 203/47 X |
| 1,884,272 | 10/1932 | Sak | 435/256 |
| 2,440,925 | 5/1948 | Boeckeler | 435/162 X |
| 3,940,492 | 2/1976 | Ehnstrom | 435/161 |

Primary Examiner—R. B. Penland
Attorney, Agent, or Firm—Davis, Hoxie, Faithfull & Hapgood

[57] ABSTRACT

A continuous process for producing ethanol by fermenting carbohydrate containing feed stocks at atmospheric pressure in a fermentor, in which a fermentation liquor stream is withdrawn from the fermentor, a yeast concentrate is recovered from said stream both recycled to the fermentor and the yeast-free remainder treated to remove ethanol and leave a stillage stream, a large portion of which is recycled to the fermentor, enabling high concentration of fermentable material to be supplied to the fermentor and reducing the amount of water required for the process.

10 Claims, 5 Drawing Figures

FERMENTATION METHOD

CROSS REFERENCE TO RELATED PATENT APPLICATIONS

This application is a continuation-in-part of my co-pending application Ser. No. 246,305 filed Mar. 23, 1981 which is a continuation-in-part of application Ser. No. 003,939 filed Jan. 16, 1979 both now abandoned.

FIELD OF THE INVENTION

This invention relates to a method for producing organic compounds such as ethanol by fermentation, in a fermentor, from a raw material with a relatively high concentration of carbohydrate.

BACKGROUND AND DESCRIPTION OF THE PRIOR ART

The main methods for the manufacture of industrial ethanol are based on either ethylene conversion or fermentation of carbohydrate containing raw materials. In spite of several modifications and improvements, the fermentation method has not been competitive for the production of ethanol for use in certain technical products, such as fuels, until the rapid change during the last decades in the price and supply of fossil raw materials.

The changing raw material situation has emphasized the importance of further improvements in the fermentation routes. In many countries having available great quantities of cheap sugar or starch-based raw materials, vigorous development work is now under way. Recent reasearch results make it possible to believe that the conversion of cellulose will be economically feasible. Cellulose is available all over the world in seemingly unlimited quantities and is a potentially ideal raw material for the production of ethanol.

Most presently existing plants for the production of ethanol by fermentation are based upon batch operation, which requires a relatively dilute input and delivers enormous amounts of waste water (i.e. stillage). If left untreated, this waste water will impose a very high biological load upon receipient streams and other bodies of water. Production of ethanol on a large scale by fermentation is feasible only if the process residue can be disposed of in an economically justifiable way without deterioration of the environment.

A continuous fermentation method has also been proposed for industrial use, which method is based upon a number of fermentor tanks coupled in a cascade configuration, with increasing ethanol concentration and decreasing substrate concentration being maintained stepwise from tank to tank. The method has not gained wide-spread use, probably due to infection problems in combination with the same disadvantageous concentration limit for the feed stream as that of the traditional batch method.

A serious drawback of the methods used hitherto for the production of ethanol by fermentation is thus related to the need for a dilute feed stream which sets severe limitations on the possibility of achieving a process residue of sufficient concentration for economical disposal. At an ethanol concentration of about 7% in the fermentor, ethanol inhibition of the fermentation process appears. In conventional processes this sets an upper practical limit for substrate concentration in the feed stream of about 16-18% fermentable carbohydrates.

Another constraint of the conventional batch methods is low ethanol productivity in relation to plant capital costs. For the purpose of raising the ethanol productivity, different methods have been suggested for maintaining a high yeast cell concentration during the fermentation. For economical reasons this means that yeast cells must be kept alive and employed for ethanol production over an extended period of time.

In U.S. Pat. No. 2,440,925 there is disclosed a method for prolonging a batch fermentation cycle and therewith the period for using the same yeast. The toxic effects on the yeast of ethanol at higher concentrations is avoided by removing ethanol during the batch run. For the removal of ethanol, liquid is withdrawn from the fermentation vessel and stripped off under vacuum to avoid the high temperatures which would cause deterioration of the yeast. From the vacuum vessel the yeast is recycled to the fermentation vessel together with the stillage in which the yeast is suspended. This undesired stillage accumulation in the fermentor, however, rapidly inhibits the yeast activity and ends the batch.

It has also been suggested that the fermentor be operated under vacuum to boil off the ethanol at a temperature low enough to maintain the yeast activity. One serious drawback inherent in this method is that all the carbon dioxide formed during the fermentation must be removed through the apparatus used for producing the reduced pressure, which results in a very high energy consumption.

An investigation reported in "Biotechnology and Bioengineering," Vol. 19, p. 1125-43 (1977) indicated that a concentrated substrate of 33% glucose could be continuously fermented, with maintenance of high yeast concentration (4-7%), in a vacuum fermentor. Ethanol is continuously boiled away from the fermentor; a bleed stream is continuously withdrawn from the fermentor to prevent accumulation of non-volatile substances in the fermentor, and yeast is recycled after having been separated from the bleed stream by settling. For industrial purposes, the replacement of the settler by a centrifuge is suggested. Despite the serious drawback mentioned above of great energy consumption for compression of carbon dioxide, the report emphasizes the use of vacuum fermentation technique because it makes possible the use of a concentrated feed stream, which as concluded in the report, would not be possible in continuous *atmospheric* fermentation.

The negative influence on yeast activity of subjecting the yeast to certain concentrations of fermentation residue (stillage), has been appreciated for many years and has deterred the adaption of stillage recycle, but it has not been very well understood or investigated. In fermentation processes for the production of yeast, reuse of fermentation residue has been practiced for the purpose of more completely utilizing nutrients in the wort, for further yeast propagation. For example, U.S. Pat. No. 1,884,272 suggests withdrawing yeast-containing wort from a propagation vessel, removing yeast be centrifugation and returning the yeast-free wort within the plant with reuse of an unspecified part of it for further propagation. Since ethanol also may be formed as by-product, the patent mentions the possibility of withdrawing yeast-free wort from time to time for ethanol recovery by distillation before returning the wort.

SUMMARY OF THE INVENTION

An object of the present invention is to provide a method for the production of ethanol by fermentation, which allows the input of a raw material of high concentration of fermentable substance thus minimizing water input and energy consumption, while allowing ethanol productivity and high yields and avoiding the economical drawbacks of vacuum fermentation.

Another object of the invention is to provide a non-vacuum fermentation method for the production of ethanol at high productivity and in a high yield, which method also gives a fermentation residue of such a high solids concentration that it can be rendered harmless or utilized in an efficient economical way.

The present invention provides a methond wherein these objects can be achieved.

Specifically the invention provides, in a system wherein a carbohydrate containing substrate is continuously fermented at about atmospheric pressure in a fermentor and a concentration of active yeast cells such as to achieve an ethanol productivity in the range of 5-20 kg/h ethanol per cubic meter fermentor liquid volume is maintained in said fermentor by continuous yeast recirculation, the improvement which comprises continuously charging into the system a feed stream containing at least 18% by weight of yeast fermentable carbohydrates, the volume of said feed stream being such as to maintain the concentration of fermentable substance in the fermentor at less than 2% by weight, continuously withdrawing a stream of the fermentation liquor from the fermentor at a flow rate to maintain an ethanol concentration of 3-7% by weight in the fermentor, continuously separating in a centrifugal separation step said stream of fermentation liquor into at least one yeast concentrate stream and an essentially yeast-free stream, continuously returning said yeast concentrate stream to the fermentor, continuously separating said yeast-free stream into an ethanol-enriched stream and a residual stream, continuously discharging said ethanol enriched stream, continuously discharging part of said residual stream and continuously heating the remaining part of said residual stream to a temperature above about 60° C. and recirculating said heated stream to the fermentor.

DETAILED DESCRIPTION OF THE INVENTION

The method according to the invention provides for the first time a general method for continuous fermentation at atmospheric pressure which makes possible the use of a feed-stock of any desired high concentration of fermentable carbohydrate and a corresponding reduction in water input. In contrast to vacuum fermentation as reported, for example, in said "Biotechnology and Bioengineering" article, the ethanol concentration in the fermentor can be maintained at a level at which no serious ethanol inhibition occurs by withdrawing a comparatively large stream of fermentation liquor from the fermentor and treating this stream, in a centrifugal separation step, to obtain a yeast concentrate stream which is recycled to the fermentor and a yeast-free stream which is treated in an ethanol separation step. To maintain a continuous steady-state operation in the fermentor, the mass balance is maintained by continuous recycling stillage to the fermentor from the ethanol separation step. By this stillage recirculation the ethanol concentration in the fermentor can be maintained at any desired low value below the limit for ethanol inhibition. If for example, in a traditional continuous ethanol fermentation, a concentration in the fermentor of 5% is maintained, the corresponding concentration limit of fermentable carbohydrates in the feed stream is about 10%, since about half of the fermentable material is converted to carbon dioxide and the other half to ethanol. On the other hand, according to the present invention a feed-stock, of for example, 30% can be supplied to the fermentor, with a stream of about 3 times the size of the feed stream continuously being withdrawn from the fermentor, and a stillage stream of about 2 times the feed stream continuously re-cycled to the fermentor to maintain a steady-state operation.

As the above simple mass balance illustrates, according to the method of the invention there is no upper limit for the concentration of fermentable carbohydrates in the feed-stock as far as the problem of ethanol inhibition in the fermentor is concerned. The only limitations with respect to the composition of the feed stream are that the amount of water continuously fed to the process circuit must provide sufficient flow properties in the different process streams, and that the steady-state concentration of soluble and osmotic non-fermentable substances in the fermentor must be at a level tolerated by the yeast.

In this context, the term "non-fermentable substance" is used for all materials contained in the feed-stock except water and the carbohydrates which are capable of fermentation to ethanol and carbon dioxide. The content and nature of "non-fermentables" differ considerably with the raw material used in the feed stream. Common raw materials for ethanol fermentation such as grain and molasses, for example, differ considerably in this respect. Thus grain is comparatively high in solid non-fermentables, while molasses contains more soluble osmotic substance. Therefore, the dilution level or the upper limit on concentration, as far as grain is concerned, is generally determined by flow requirements, while in case of molasses, the steady-state concentration of soluble osmotic salts in the fermentor may put a lower limit on the water content of the feed stream. For this reason the upper limit of fermentable concentration in the case of grain might be about 35% by weight; for pure starch, about 70% by weight.

In addition to the general new concept according to the present invention which enables ethanol inhibition to be avoided while still feeding a concentrated substrate, by withdrawing a large stream of fermentation liquor from the fermentor and continuously recycling stillage, the method also provides fundamentally improved conditions for avoiding bacterial infection in the fermentor.

Some of the fundamental differences between the continuous vacuum fermentation method reported in the "Biotechnology and Bioengineering" referred to above and the present invention can be illustrated by the following illustrative mass balance calculations:

Assume for both the continuous vacuum fermentation, and the continuous atmospheric fermentation according to the present invention, a fermentor liquid volume of $Vm^3$, a feed stream containing 30% by weight fermentables (F) and 10% non-fermentables (NF) (the balance being water) and an ethanol productivity of 10 kg/h/$m^3$ fermentor liquid volume. Further, assume a steady-state concentration of NF in the fermentor of 20% by weight. For simplicity, a density of 1000 kg/$m^3$ is assumed for all liquid streams.

Vacuum fermentation

From the asseumed ethanol productivity, the ethanol produced will be 10 V kg/h. An equal amount of $CO_2$ is produced, i.e. 10 kg/h. Thus the total fermentables required in the feed stream will be 20 V kg/h. At a concentration of 30% the volume of the feed stream will be 20V/0.3 kg/h = $10^{-3}$·20V/0.3 m³/h = V/15 m³/h.

Since the bleed required to balance the input of non-fermentables contains 20% NF (concentration of NF in the fermentor) and the feed stream contains 10% NF, the bleed stream will be about V/30 m³/h. Thus, in terms of the foregoing simplified calculation the average residence time for a non-volatile non-fermentable in the fermentor is about 30 hours.

Atmospheric fermentation according to the invention

If 5% by weight ethanol is selected as the desired concentration in the fermentor, and 10 V kg/h ethanol must be continuously discharged, at least 10 V/0.05 kg/h yeast-free fermentation liquor must be sent to the ethanol separation step, i.e. 200 V kg/h. Since a density of 1000 kg/m³ is supposed, the yeast-free stream will be on the order of V/5 m³/h. Further, if the volume of the yeast concentrate stream recycled to the fermentor is of the same order as the yeast-free stream sent to the distillation step, the total stream continuously withdrawn from the fermentor will be on the order of V/2.5 m³/h. Thus, according to the simplified calculations, one fermentor liquid volume is fed to the centrifugal separation step every 2.5 hours and one fermentor liquid volume of yeast-free liquor is passed to the ethanol separation step every 5 h. The stillage stream to be discharged is, as in the vacuum case, V/30 kg/h, and if the ethanol enriched vapour stream distilled off at the ethanol separation step is assumed to be concentrated from 5% by weight to about 30% by weight, the ethanol vapor stream discharged from the process will be about V/30 kg/h. Consequently, the stillage stream to be recycled to the fermentor is V/5 − V/30 − V/30 = 4V/30 kg/h. This means that 1/5 of the total stillage stream is discharged while 4/5 is recycled to the fermentor.

The above simplified calculation illustrates an important and unique feature of the present invention: The fermentation liquid has a very short average residence time in the fermentor (3–6 hours) before the yeast-free fraction of the fermentation liquor reaches the ethanol separation step. When distillation is used for ethanol separation this means that bacteria in this stream are effectively killed off and because of the short residence time bacteria do not have a chance to propagate. It should be emphasized that such a brief average residence time between charging and distillation has not been possible in any method of the prior art.

To achieve a substantive bacteria reducing effect on the yeast-free fermentation liquor, the liquor should be subjected to a temperature of at least 60° C. In case of separating the yeast-free liquor by distillation at about atmospheric pressure, the temperature in the base of the distillation column will be in the range of 100°–115° C., and a normal residence time of a few minutes in the distillation unit provides a sufficient bacteria reducing effect. There is of course no upper temperature limit in this context, since the reduction of the viable bacteria population will be more complete the higher temperature that is employed.

Even if another separation technique is used, such as an extractive method, the stillage to be recycled to the fermentor can be subjected to bacteria reduction by heat treatment since the heat sensible yeast has already been separated and returned to the fermentor.

Further, it should be noted with respect to the infection problem, that the effect of the short residence time in the fermentor is reinforced by the high concentration of osmotic non-fermentables in the fermentor, which is the result of the use of a highly concentrated feed-stock. This combination of a difficult environment for bacterial growth in the fermentor and a short residence time is an important and unique feature of the invention.

With respect to the infection problem, a further beneficial effect has been noted in the use of certain types of centrifuges in the yeast separation step. Preferably, centrifugal separators of so called nozzle-type are used. In such machines the fermentor effluent is separated into two phases. The heavier phase, which is the yeast cell concentrate, is taken out through nozzle openings in the rotor periphery and a lighter yeast-free phase, that can contain other suspended particles lighter than the yeast cells, for example proteins and bacteria, is taken out closer to the center of the separator. As it develops the bacteria have a tendency to be selectively withdrawn in the yeast-free stream which is sent to the distillation unit. There they are rendered harmless by the elevated temperature.

It is important to maintain a low concentration of fermentable carbohydrates in the fermentor to avoid losses in the discharged stillage. Therefore, it was also an important discovery that high ethanol productivity obtained by the yeast recycling system according to the invention was compatible with a carbohydrate concentration in the fermentor of less than 2% and generally less than 0.5%. The lower limit for said concentration is an economic consideration and in theory the concentration can approach zero. However, lower concentration requires a larger fermentor volume, and in practice, sugar concentrations in the range 0.05–0.2% are compatible with reasonable fermentor volumes.

The low steady-state concentration of fermentable sugar in the fermentor is reflected in the overall process yield. It has been found that during fermentation of raw materials requiring enzymatic degradation, such as grain, certain degradation products can be further fermented to ethanol only if the glucose concentration in the fermentor is sufficiently low. Also, by maintaining a low concentration of fermentable sugar in combination with a considerable ethanol concentration the production of by-products, especially glycerol, is minimized.

The ethanol concentration is maintained in the range 3–7% by weight, and a selected steady-state value can easily be maintained or changed by controlling the fermentor effluent stream and the stillage recirculation stream. The lower practical limit is set by energy costs. Too low an ethanol concentration in the stream sent to the distillation unit will be economically disadvantageous. The upper limit is set by the inhibiting effect of the ethanol. Even at 7% ethanol, longer fermentation times are required which means that larger fermentor volume is needed to maintain a certain ethanol production. The concentration of ethanol in the fermentor which is selected depends upon the nature of the substrate and yeast.

A yeast cell concentration in the range of $10^8$–$10^9$ cells/ml is maintained in the fermentor by recycling yeast separated from the fermentor effluent stream and controlling the yeast growth by injecting air into the fermentor liquor. Due to the high degree of yeast adaptation that is possible in a steady-state system, a low yeast growth rate, consuming less than 1% of the fermentable material, will be sufficient to maintain the desired ethanol productivity. In the conventional batch system normally about 5% of the fermentable material is consumed for the cultivation of new yeast to replace spent yeast.

In many applications of the invention the mash to be fermented contains insoluble material in form of particles that can cause operational disturbances or interruptions in the fermentation loop. In particular, such particles will accumulate in the rotor of the centrifugal separator due to their large particle diameter in relation to the nozzle openings.

To avoid this problem the particles can be separated during substrate preparation so that a "clear mash" is fed to the fermentation loop. Such a pre-separation of the mash makes a screening operation difficult since the particles to be screened stick to the screen surface. Further, the screened particle fractions will contain a certain amount of fermentable sugar, either causing losses or requiring additional laborious washing procedures.

Therefore, one advantageous embodiment of the present invention is the insertion of one or several screening steps in the fermentation circuit after the fermentor. Suitably, the fermentation liquid discharged from the fermentor is screened before being fed to the centrifuge and the particles screened off by-pass the centrifuge and rejoin the yeast-free flow leaving the centrifuge. Conical centrifugal sieves or bow sieves having 150–200 $\mu$m sieve openings can be used for this purpose.

In such a way, no losses of fermentable material are suffered and no washing step to recover sugar from the particles screened off is needed. The ethanol accompanying the screened particle fraction will be automatically distilled off in the subsequent distillation step. Any minor yeast portion screened off with the particles can easily be recovered by washing the sludge phase with yeast-free liquid, for example with part of the yeast-free flow from the separator.

The incorporation of the screening step in the fermentation liquid circuit also brings an additional advantage connected with protein separation in the centrifugal separator. During the screening operation fibres are mainly removed, that is the husk parts when cereals are used as raw material, while the yeast and the protein particles pass to the centrifugal separator. Although the yeast density is only slightly higher than that of the proteins, the proteins can nevertheless be separated from the yeast phase without excessive yeast losses because a sufficiently high flow can now be maintained in the separator. The proteins are then denatured by heat treatment in the subsequent distillation step to form aggregates which are more suited to be separated off together with the fibre fraction at subsequent screening.

For separating ethanol from the yeast-free fermentation liquor, different methods can be employed. Besides the traditional distillation method, solvent extraction has been investigated by the inventors in laboratory experiments. However, even though several solvent extraction systems have proved to be operable, no such system has yet been found competitive with the distillation method. Other separation methods under investigation are based upon absorption, adsorption and reverse osmosis.

According to a preferred embodiment of the invention, the yeast-free stream from the yeast separation step is released from almost all its ethanol content in a distillation unit. This unit can be an ordinary distillation column with a sufficient number of trays to provide an overhead ethanol-water vapor containing 25–50% by weight ethanol. By establishing, through indirect heating, a temperature in the bottom part of the column above 60° C., the stillage stream passing through the column is subjected to pasteurization. The high concentration of soluble non-fermentable substance, being an important feature of the present invention, affects the liquid-vapor equilibrium positively to increase the ethanol-water ratio in the withdrawn vapor. When carbohydrate raw materials are used that require enzymatic degradation into fermentable sugar, it can be advantageous to integrate the saccharifying step with the ethanol fermentation step. If a partial vacuum is used in the distillation column to maintain the bottom temperature in the range of 60° C., the pasteurizing effect is compatible with the preservation of the degradation enzymes recycled with the stillage recycling stream.

Instead of indirect heating, steam can be utilized directly in the distillation step without changing the basic concept of charging minimum water to the system. During grain fermentation, for example, the recycled stillage can be used for dilution during the starch liquifaction step and the water charge otherwise necessary at this step can be reduced with an amount corresponding to the steam input to the distillation unit.

The important concept of achieving a fermentation process in which the concentration of the feed is determined generally by the amount of soluble non-fermentable substance and not, as was the conventional concept, by the amount of fermentable substance, provides, within the limits of said new concept, the possibility of supplying a more concentrated feed that the conventional limit of 16–18% fermentables, reducing the water flow through the process, and achieving a much more concentrated stillage to be disposed of. It should be observed, that the DS (dry solids) content of the stillage taken out from the distillation unit is, without further concentration, about 15% higher than the steady-state DS content in the fermentor, and as can be concluded from the discussion above, the part of the total DS content of the fermentor liquor related to soluble material alone can be brought up to a value in the range of 12–18% depending on the yeast strain and raw material employed. It is also easily realized that during the fermentaion according to the invention of a raw material having a low content of soluble non-fermentable substance, a large recirculation stream and a minor stillage discharge stream can be maintained, the stillage being many times more concentrated as to non-fermentable substance than the feed stream. In any case, the invention provides the possibility of obtaining a waste flow which can be further processed economically to valuable products, such as animal feedstuff, or be used for combustion.

Even if the building-up in the circuit of solids over a certain steady-state concentration is prevented by means of stillage discharge, this concentration can be quite high, for example when unscreened grain mash is fermented. Therefore it can be advantageous to separate off particles and fibres from the stillage before recycling, thereby reducing the inert solid load of the whole recirculation system. Further, when such raw materials are used for which, due to high solid content, minimum feed dilution is determined by fluidity requirements rather than by the upper concentration limit of soluble substance in the fermentor, there may remain a further margin up to said limit which can be utilized for further mechanical concentration of the stillage portion to be discharged. Single or combined operations such as screening, pressing and centrifugal separation can be used for this purpose.

The continuous method according to the invention means a considerable step forward towards simplified equipment and simplified process control within the fermentation art. Thus, one fermentor, simplified piping, a simple control system and minimum cleaning requirements are to be compared with the complex system of a battery of fermentor tanks, propagation and storage tanks, piping and valves in the conventional batch process.

A further advantage inherent in the unique system of maintaining, through the whole fermentation circuit, a very low concentration of fermentable substance, is that if as a consequence of unforeseen operational disturbances, for example, the whole fermentor content must be emptied, it can be done through the distillation unit without any loss of valuable raw material.

Since the fundamentally new fermentation method of the present invention has been described in view of prior art dominated by traditional fermentation of carbohydrates by means of yeast, the term "yeast" has been used for reasons of simplicity throughout the specification and claims. However, the present invention includes the use of other microorganisms than those generally referred to as "yeasts". For example, excellent ethanol fermentation by means of the bacterium strain *Zymomonas mobilis* has been carried out by applicant. This microorganism showed osmosis tolerance and ethanol inhibition characteristics similar to those described above for different yeast strains. Also, the size of such alcohol fermentation bacteria, being in the range of 1-2 and comparable to the size of common yeast cells of 5-8 $\mu$m, permits efficient separation from the beer liquor by means of centrifugal separation.

The method of the invention will be further described with reference to the accompanying drawings, in which.

Figure 1:
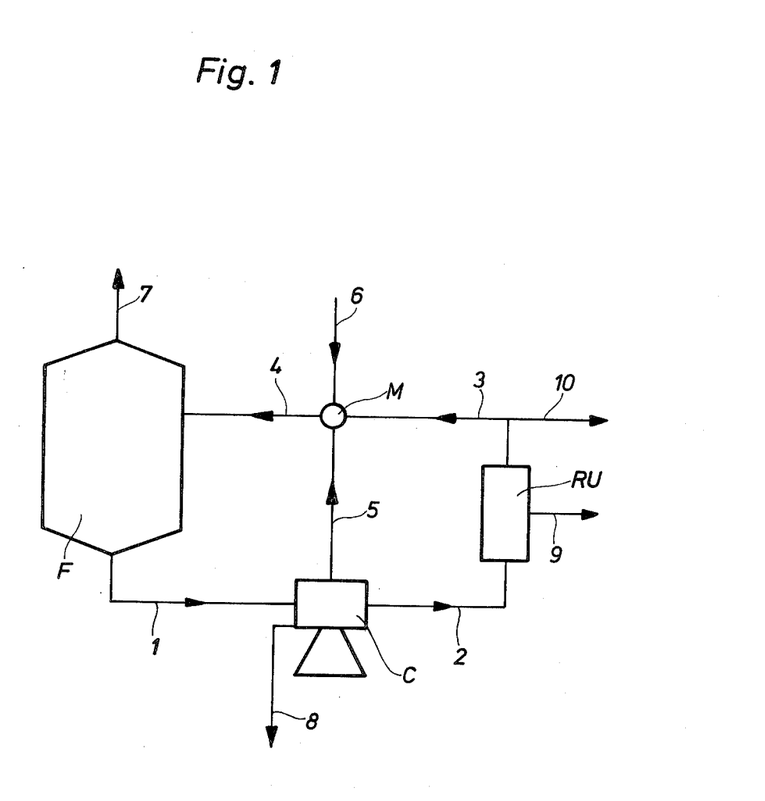
FIG. 1 is a principal flow sheet of the method according to the invention.

The system shown in FIG. 1 comprises a fermentor F, a centrifugal separator C, a separation unit SU for removal of ethanol from the yeast-free beer, and a mixer M. A feed inlet line 1 is connected to the mixer M. Fermentor F is provided with a gas outlet 2 and a beer outlet line 3 connected to separator C. The centrifugal separator C separates the incoming beer into a yeast concentrate flow 4, which is returned to the fermentor F and an essentially yeast-free stream 5 which is sent to the separation unit SU. In the separation unit SU the yeast-free stream 5 is separated into an ethanol enriched stream 6, which is discharged, and a stillage stream 7.

The stillage stream 7 is divided into a stillage discharge stream 8 and a stillage recirculation stream 9 which is returned to mixer M. Also, if the separator C employed is a centrifuge equipped for intermittent sludge discharge, such a sludge stream, marked by line 11, can be either discharged or recirculated in the circuit.

Figure 2:
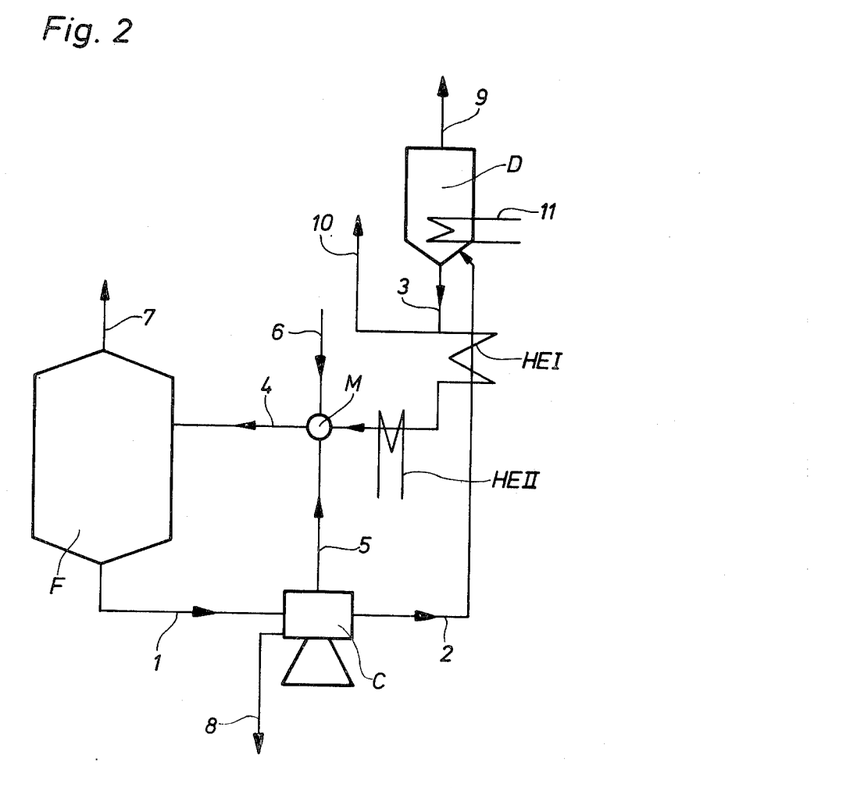
FIG. 2 is a flow sheet of the method carried out with distillative separation of ethanol in the yeast-free beer.

One embodiment of the method is shown in FIG. 2, in which figure the same reference notations have been used as in FIG. 1 for corresponding apparatus units and lines. A feed stream 1, which, for example, may be a liquified grain-water mixture, is continuously fed to a saccharifying unit SAC. From unit SAC a stream 1a of saccharified substrate is fed to the fermentation circuit through mixer M.

The beer outlet stream 3 from fermentor F is screened by means of a screening device SI, from which a beer flow 3a free from larger particles and fibres is sent to separator C, which is preferably a centrifuge of the nozzle-type. A solid enriched portion 3b from the screening device SI is rejoined with a yeast-free stream 3c from separator C into a stream 5 which is sent to a distillation unit D.

In the distillation unit D which comprises at least one indirectly heated distillation column, the stream 5 is separated into an overhead ethanol containing vapor stream 6 and a bottom stillage stream 7. A minor portion of stillage stream 7 is discharged in a stream 8 and the remaining stillage portion is recirculated in a stream 9 to fermentor F through mixer M.

The recirculated stillage stream is used for heating, in a heat exchanger HE I, the stream 5 before it is fed to the distillation Unit D. A cooler HE II is used to control the fermentor liquor temperature.

Figure 2A:
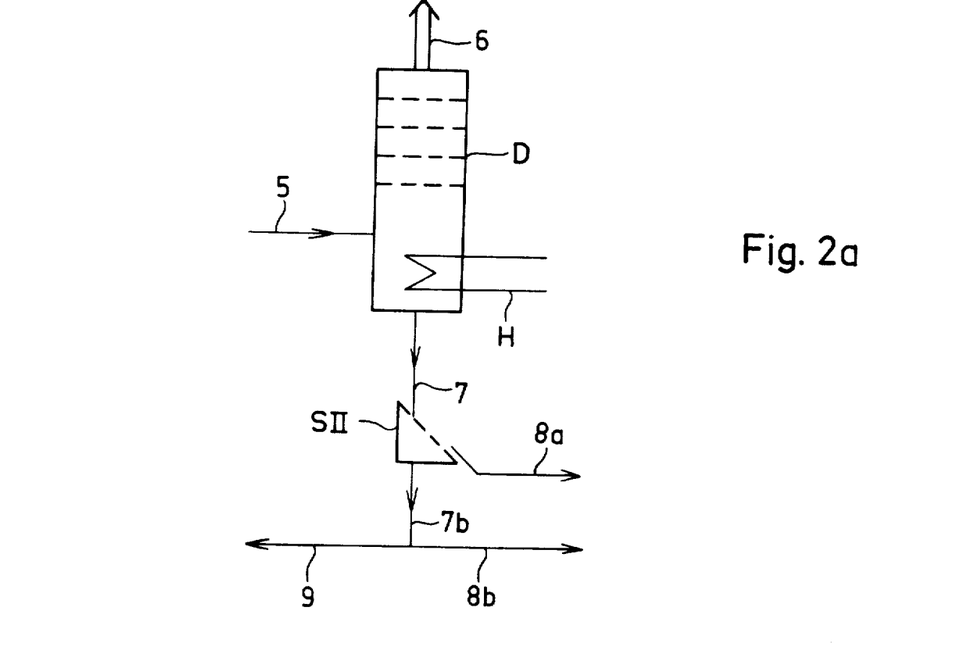
FIG. 2a a partial flow sheet of the method shown in FIG. 2, but showing an alternative stillage treatment.

In FIG. 2a an additional stillage treatment in the method according to FIG. 2 is shown. The same reference notations have been used as in FIG. 2 for corresponding apparatus units and lines. A screening device S II, suitably a conical centrifugal sieve or a bow sieve, is inserted in the stillage line 7 coming from distillation unit D. Such a screening operation serves to reduce the inert solid load of the fermentation recirculation circuit and to further concentrate the stillage portion to be discharged. From the screening step S II the stillage portion, enriched with solids, is discharged as a stillage concentrate flow 8a. The stillage portion 7b that passes through the sieve openings is wholly or partially recirculated as a stillage recirculation stream 9 to the fermentor F. If the water content of the stillage concentrate stream 8a is not sufficient to carry with it enough soluble non-fermentable substrate to balance the amount of this substance fed to the fermentation circuit, a part of the clarified stillage stream 7b also has to be discharged as an additional stillage discharge stream 8b.

Figure 2B:
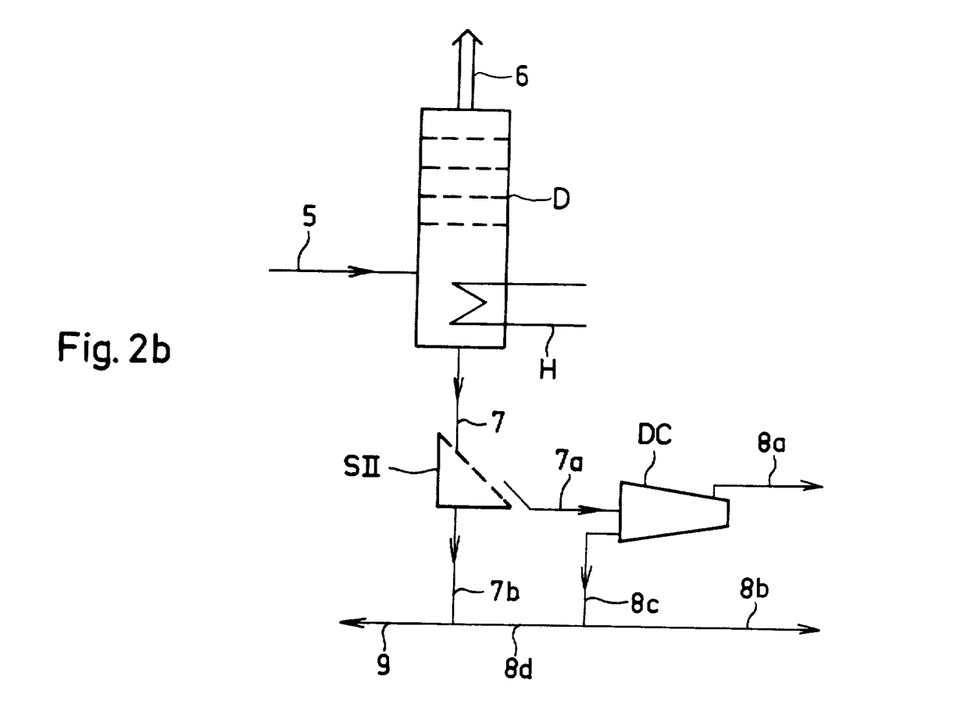
FIG. 2b is a partial flow sheet of the method shown in FIG. 2, but showing a further alternative stillage treatment.

In FIG. 2b a further alternative stillage treatment is shown. In the figure the same reference notations have been used as in FIG. 2 for corresponding apparatus units and lines. Similar to the embodiment of FIG. 2a, the stillage stream 7 from the distillation unit DC is screened by means of a screening device S II. The solid-enriched stillage portion 7a is further concentrated in a decanter centrifuge DC to a stillage concentrate 8a. The claified liquid 8c leaving the decanter DC can be recirculated as a stream 8d to the fermentation circuit, provided sufficient soluble non-fermentable material is withdrawn with the stillage concentrate discharge 8a. Otherwise, whole or part of the effluent stream 8c has to be discharged as a clarified stillage discharge stream 8b.

This clear stillage may be further concentrated in a suitable evaporator unit.

Figure 3:
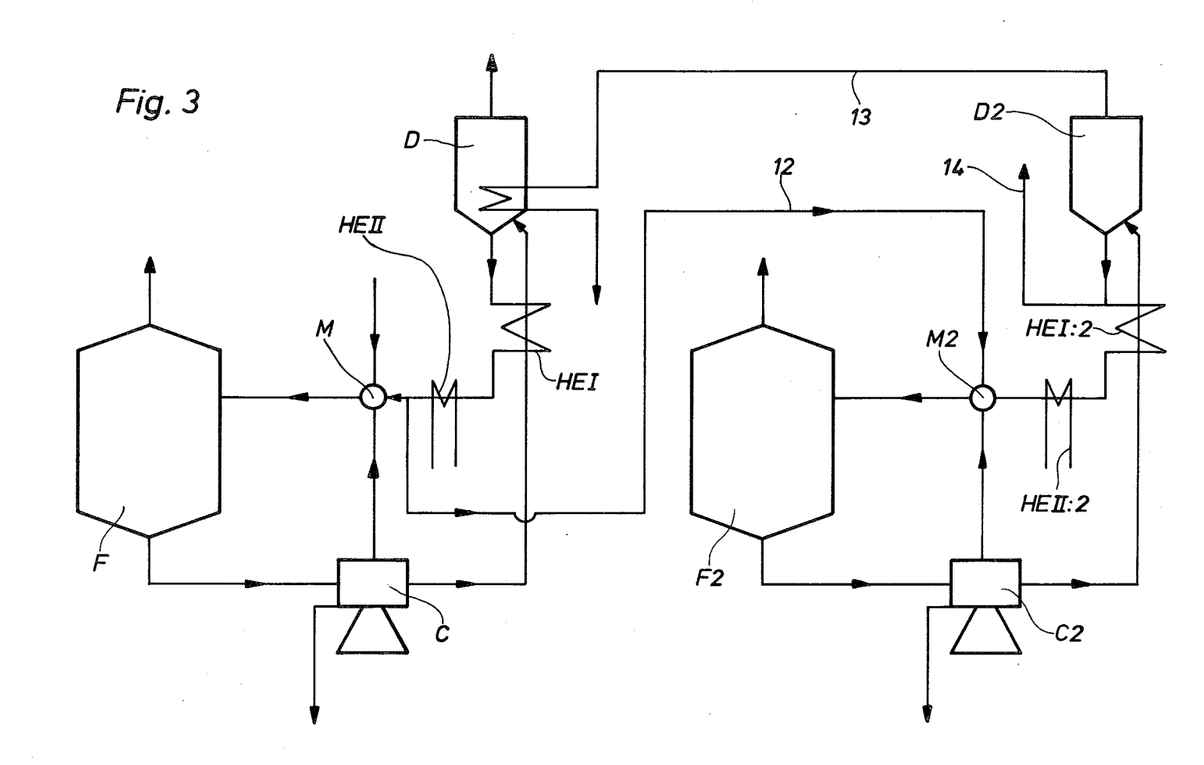
FIG. 3 is a flow sheet of the method similar to FIG. 2, but showing direct heating of the distillation unit.
Figure 4:
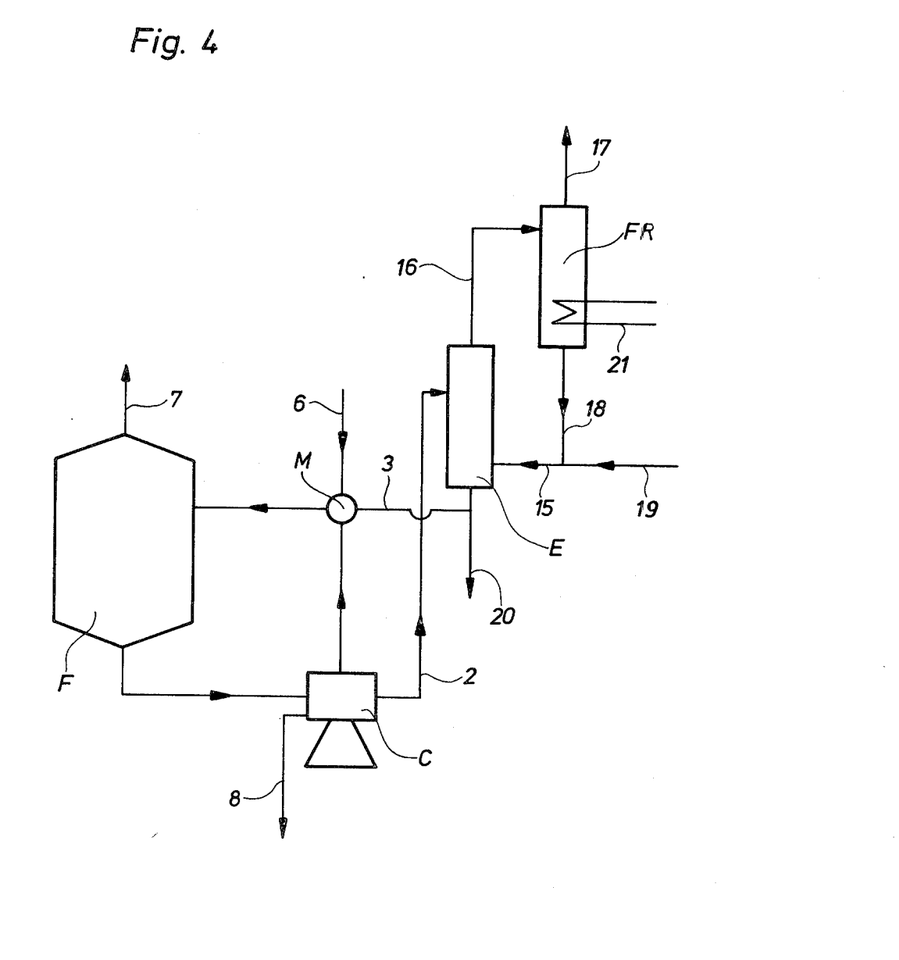

FIG. 3 shows an embodiment similar to that of FIG. 2 but includes certain modifications. The same reference notations have been used as in FIG. 2 and FIG. 2b for corresponding apparatus units and lines. For heating the distillation unit D direct stream 10 is used. This does not mean any additional dilution of the material flow in the fermentation circuit, but may be considered as an alternative way of feeding the process water needed in the system. Thus, the steam 10 replaces the corrresponding amount of water that otherwise, during indirect heating of the distillation unit, would have been contained in the feed stream 1 to saccharifying unit SAC. An advantage of using direct steam in the distillation unit is that heat transfer surfaces are avoided.

To wash out minor amounts of yeast accompanying the solid-enriched portion screened off in the screening step S I, a minor portion 3d of yeast-free stream 3c from the separator C is used. To reduce the solid load of the fermentation circuit and further concentrate the stillage to be discharged, the same combination of screening and further concentration, by means of a decanter centrifuge as described in FIG. 2b, is used.

The following fermentation examples further demonstrate the advantages and special features of the invention.

EXAMPLE 1

Cane molasses was continuously fermented under steady-state conditions in a process circuit shown in FIG. 2 with the exception that the saccharifying step SAC was excluded. The fermentor was kept under atmospheric pressure. The pH and temperature of the fermentor liquid was controlled at about 4.5° and 32° C., respectively. The yeast growth was controlled by air injection. The yeast *Schizosaccharomyces pombe* was used.

The following total feed stream 1a was charged:

|  | kg/h | % by weight |
| --- | --- | --- |
| Fermentable material | 56 | 23 |
| Non-fermentable soluble material | 22 | 9 |
| Non-fermentable solid material | 2 | 1 |
| Water (total) | 163 | 67 |
|  | 243 | 100 |

The essentially yeast-free stream 5 from the separator C fed to the distillation column D was 580 kg/h and the stillage stream 9 recirculated to the fermentor F was 363 kg/h and having substantially 0% ethanol concentration. From the distillation column D 65 kg/h vapor containing 38% ethanol was withdrawn, and from the fermentor 26 kg/h carbon dioxide was released.

The following steady-state conditions were maintained in the fermentor F:

| Yeast | $5 \cdot 10^8$ cells/ml |
| --- | --- |
| Air | 0.1 ppm |
| Ethanol | 4.3% |
| Total DS (except yeast) | 15% |
| Fermentable sugar | 0.2% | a stillage stream 8 of 152 kg/h and a total DS content of 17% by weight was continuously discharged.

EXAMPLE 2

As raw material for ethanol fermentation, wheat (87%DS) was used. The example is related to the process circuit shown in FIG. 2 and stillage screening according to FIG. 2a. The fermentor was kept under atmospheric pressure, pH in the fermentor was controlled at about 4.5 and the fermentation temperature was kept at 32° C. To avoid larger particles contained in the effluent stream 3 from the fermentor to pass the separator C and to screen off such particles from the stillage stream 7 leaving the distillation column D, centrifugal sieves S I and S II having 200 μm sieve openings were used. The yeast employed was *Saccharomyces cerevisiae*.

The following amounts of wheat raw material and water were continuously fed to the saccharifier SAC:

|  | kg/h | % by weight |
| --- | --- | --- |
| Fermentable material | 62 | 30.6 |
| Non-fermentable soluble material | 10 | 4.9 |
| Non-fermentable solid material | 15 | 7.4 |
| Total water | 116 | 57.1 |
|  | 203 | 100.0 |

The stream 5 fed to the distillation column D including the yeast-free stream 3c from the separator C as well as the by-pass stream 3b was 530 kg/h, and the stillage stream 9 recirculated to the fermentor F was 360 kg/h (ethanol concentration close to 0). From the distillation column D 69 kg/h vapor containing 42% by weight ethanol was withdrawn, and from the fermentor 33 kg/h carbon dioxide was released.

The following steady-state conditions were maintained in the fermentor F:

| Yeast | $5 \cdot 10^8$ cells/ml |
| --- | --- |
| Air | 0.015 ppm |
| Ethanol | 5.5% |
| Total DS (except yeast) | 16% |
| Fermentable sugar | 0.05% |

The amount of stillage continuously discharged through the streams 8a and 8b were together 101 kg/h, and the total solid content of these streams was 26% by weight.

EXAMPLE 3

A similar fermentation run to that of Example 2 was carried out on wheat. The same process equipment was used with the exception that stillage treatment according to FIG. 2b, including a decanter centrifuge, was employed. The yeast strain and other fermentation conditions were the same as in Example 2.

The following substrate mixture was fed to the saccharifier SAC:

|  | kg/h | % by weight |
| --- | --- | --- |
| Fermentable material | 62 | 31.8 |
| Non-fermentable soluble material | 10 | 5.1 |
| Non-fermentable solid material | 15 | 7.7 |
| Total water | 108 | 55.4 |
|  | 195 | 100.0 |

The stream 5 fed to the distillation column D was 130 kg/h and the stillage stream 9 recirculated to the fermentor F was 368 kg/h. From the distillation column D, 69 kg/h vapor containing 42% ethanol was withdrawn, and 33 kg/h carbon dioxide was released from the fermentor.

Steady-state conditions in fermentor F:

| | |
|---|---|
| Yeast | $5 \cdot 10^8$ cells/ml |
| Air | 0.015 ppm |
| Ethanol | 5.5% |
| Total DS (except yeast) | 17% |
| Fermentable sugar | 0.04% |

The amount of stillage continuously discharged, i.e., the total of the sludge phase 8a discharged from the decanter centrifuge DC and the further bleed stillage stream 8b was 93 kg/h and an over-all DS content in the discharged stillage of 30% was reached.

EXAMPLE 4

Continuous grain (85% DS) fermentation was carried out under steady-state conditions in a process circuit similar to that of FIG. 3. The fermentation environment was controlled according to Example 2. The yeast employed was saccharomyces cerivisiae.

The following material flow was charged to the system with feed flow 1 and vapor flow 10:

| | kg/h | % by weight |
|---|---|---|
| Fermentable material | 60 | 31.6 |
| Non-fermentable soluble material | 7 | 3.7 |
| Non-fermentable solid material | 18 | 9.5 |
| Water with flow 1 | 30 | 15.8 |
| Steam to distillation unit | 75 | 39.4 |
| | 190 | 100.0 |

The stream 5 sent to the distillation column D was 598 kg/h, and the stillage stream 9 recirculated to the saccharifying unit SAC was 514 kg/h. 75 kg/h of 40% ethanol vapor was withdrawn from the distillation column D.

The following steady-state conditions were maintained in the fermentor F:

| | |
|---|---|
| Ethanol | 5.0% |
| Soluble DS | 12% |
| Fermentable sugar | 0.06% |

The stillage stream 7 from the distillation unit D was screened by means of a bow sieve and 125 kg/h solid concentrate from the sieve was charged to a decanter centrifuge. From the decanter 84 kg/h stillage concentrate of about 30% DS was discharged through the decanter sludge outlet. The decanter effluent stream was recycled together with the screened stillage liquid to the saccharifying unit.

What I claim is:

1. In the production of ethanol by the continuous fermentation of a carbohydrate containing substrate at about atmospheric pressure in a continuous process circuit comprising a fermentor in which an amount of active yeast cells sufficient to achieve an ethanol productivity in the range of 5–20 kg/h ethanol per cubic meter of fermentor liquid volume is maintained by continuous yeast recirculation, the improvement which consists essentially of continuously charging into said process circuit a feed stream containing at least 18% by weight of yeast-fermentable carbohydrates, having a concentration and flow rate sufficient to supply yeast fermentable carbohydrates in accordance with said ethanol productivity to maintain a steady state concentration of fermentable substance in the fermentor at less than 2% by weight, continuously withdrawing a stream of fermentation liquor from the fermentor at a flow rate sufficeint to maintain a steady state ethanol concentration in the fermentor in the range of 3–7% weight, continuously separating said stream of fermentation liquor, in a centrifugal separation step, into at least one continuous yeast concentrate stream and an essentially yeast-free stream, continuously returning said yeast concentrate stream to the fermentor, continuously separating said yeast-free stream into an ethanol-enriched stream, and a residual stream, continuously discharging said ethanol enriched stream from the circuit, continuously discharging part of said residual stream from the circuit in an amount sufficient to balance the amount of non fermentable substances charged to the circuit, heating the remaining part of said residual stream to at least about 60° C. and continuously recirculating said heated part of said residual stream to the fermentor.

2. The method of claim 1, further consisting essentially of distilling the yeast-free stream to effect its separation.

3. The method of claim 1, further consisting essentially of screening said stream of fermentation to form a reject fraction and a screened fraction, conveying said screened fraction to said centrifugal separation step, and returning said reject fraction to the circuit downstream of said centrifugal separation step.

4. The method of claim 1, further consisting essentially of mechanically separating said residual stream into a first fraction enriched in solid substance, and a second fraction with reduced solid content, discharging said first fraction from the circuit and returning at least part of said second fraction to the fermentor.

5. The method of claim 4, further consisting essentially of further separating said first fraction enriched in solid substance in a mechanical thickening step, into a third fraction further enriched in solid substance, and a fourth fraction poor in solids, discharging said third fraction from the circuit and returning to the fermentor at least a part of said fourth fraction.

6. The method of claim 5 further consisting essentially of thickening said first fraction in a decanter.

7. The method of claim 1, further consisting essentially of saccharifying the feed stream in a saccharifying step and returning at least part of said remaining part of said residual stream to said saccharifying step.

8. The method of claim 2, further consisting essentially of charging direct steam to said distillation step as a heating medium.

9. The metod of claim 1, further consisting essentially of maintaining a concentration of fermentable substance in the fermentor less than 0.5% by weight.

10. The method of claim 9 further consisting essentially of maintaining said concentration at less than 0.2% by weight.

* * * * *

UNITED STATES PATENT AND TRADEMARK OFFICE
CERTIFICATE OF CORRECTION

PATENT NO. : 4,460,687
DATED : JULY 17, 1984
INVENTOR(S) : LARS KARL JOHAN EHNSTROM

It is certified that error appears in the above—identified patent and that said Letters Patent is hereby corrected as shown below:

Claim 1, column 14, line 12, "3-7% weight" should be --3-7% by weight--.

Claim 3, line 31, "fermentation" should be --fermentation liquor--.

Signed and Sealed this

Seventh Day of May 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO. : 4,460,687

DATED : Jul. 17, 1984

INVENTOR(S) : Lars K. J. Ehnstrom

It is certified that error appears in the above-identified patent and that said Letters Patent is hereby corrected as shown below:

The title page should appear as shown on per attached title page.

The sheets of drawings containing Figs. 1-4 should be deleted to be replaced with Figs. 1-5 as shown on the attached sheets.

Signed and Sealed this

Twenty-fifth Day of June 1985

[SEAL]

Attest:

DONALD J. QUIGG

Attesting Officer

Acting Commissioner of Patents and Trademarks

United States Patent [19]

Ehnström

[11] Patent Number: 4,460,687
[45] Date of Patent: Jul. 17, 1984

[54] FERMENTATION METHOD

[75] Inventor: Lars K. J. Ehnström, Tullinge, Sweden

[73] Assignee: Alfa Laval AB, Tumba, Sweden

[21] Appl. No.: 532,042

[22] Filed: Sep. 14, 1983

Related U.S. Application Data

[63] Continuation-in-part of Ser. No. 246,305, Mar. 23, 1981, abandoned, which is a continuation-in-part of Ser. No. 3,939, Jan. 16, 1979, abandoned.

[51] Int. Cl.³ .................................................. C12P 7/06
[52] U.S. Cl. ...................................... 435/161; 435/162; 435/813
[58] Field of Search ................ 435/161, 162, 165, 256, 435/813; 426/31, 53, 429, 431, 493, 494

[56] References Cited

U.S. PATENT DOCUMENTS

| 504,074 | 8/1893 | Bradley et al. | 203/47 X |
| 1,884,272 | 10/1932 | Sak | 435/256 |
| 2,440,925 | 5/1948 | Boeckeler | 435/162 X |
| 3,940,492 | 2/1976 | Ehnstrom | 435/161 |

Primary Examiner—R. B. Penland
Attorney, Agent, or Firm—Davis, Hoxie, Faithfull & Hapgood

[57] ABSTRACT

A continuous process for producing ethanol by fermenting carbohydrate containing feed stocks at atmospheric pressure in a fermentor, in which a fermentation liquor stream is withdrawn from the fermentor, a yeast concentrate is recovered from said stream both recycled to the fermentor and the yeast-free remainder treated to remove ethanol and leave a stillage stream, a large portion of which is recycled to the fermentor, enabling high concentration of fermentable material to be supplied to the fermentor and reducing the amount of water required for the process.

10 Claims, 5 Drawing Figures